United States Patent
Suh et al.

(10) Patent No.: US 6,809,188 B1
(45) Date of Patent: Oct. 26, 2004

(54) METHOD OF PREPARING CLARITHROMYCIN

(75) Inventors: Kwee-Hyun Suh, Incheon-si (KR); Mi-Ra Seong, Yongin-si (KR); Nam-Du Kim, Osan-si (KR); Gwan-Sun Lee, Seoul (KR)

(73) Assignee: Hanmi Pahrm. Co., Ltd., Kyungki-Do (KR)

( * ) Notice: Subject to any disclaimer, the term of this patent is extended or adjusted under 35 U.S.C. 154(b) by 0 days.

(21) Appl. No.: 10/129,419

(22) PCT Filed: Nov. 23, 2000

(86) PCT No.: PCT/KR00/01349

§ 371 (c)(1),
(2), (4) Date: May 1, 2002

(87) PCT Pub. No.: WO01/38340

PCT Pub. Date: May 31, 2001

(30) Foreign Application Priority Data

Nov. 24, 1999 (KR) ......................... 1999/52371

(51) Int. Cl.[7] .............................................. C07H 17/08
(52) U.S. Cl. .......................... 536/7.2; 536/7.3; 536/7.4; 536/7.5
(58) Field of Search ........................... 536/7.2, 7.3, 7.4, 536/7.5

(56) References Cited

U.S. PATENT DOCUMENTS 5,864,023 A * 1/1999 Ku et al.

OTHER PUBLICATIONS

Ku et al., "An Efficient Synthesis of Des–N–Methyl–N–Acetyl Erythromycin Derivatives via the N–Oxide", Bioorganic & Medicinal Chemistry Letters, vol. 7, No. 9, pp. 1203–1206, May 1197.*

Hill et al., "Novel Macrolides via Meso–Tetraarylmetalloporphyrin Assisted Oxidations", Tetrahedron Letters, vol. 37, No. 6, pp. 787–790, Feb. 1996.*

* cited by examiner

Primary Examiner—James O. Wilson
Assistant Examiner—Traviss C. McIntosh, III

(57) ABSTRACT

Clarithromycin can be easily prepared by reacting erythromycin A N-oxide with a methylating agent to obtain 6-O-methylerythromycin A N-oxide; and treating 6-O-methylerythromycin A N-oxide obtained above with a reducing agent in a high yield.

9 Claims, No Drawings

METHOD OF PREPARING CLARITHROMYCIN

CROSS REFERENCE TO RELATED APPLICATION

This application is a National Stage Application of International Application Number PCT/KR00/01349, filed Nov. 23, 2000.

FIELD OF THE INVENTION

The present invention relates to a method of preparing clarithromycin using erythromycin A N-oxide; and to a novel intermediate prepared in said method.

BACKGROUND OF THE INVENTION

Clarithromycin, 6-O-methylerythromycin A, is a semi-synthetic macrolide antibiotic which exhibits a wide range of antibacterial activity against gram positive bacterium, some gram negative bacterium, anaerobic bacterium, Mycoplasma, Chlamidia and *Helicobacter pylori* (see U.S. Pat. No. 4,331,803).

Clarithromycin can be prepared by methylating the 6-hydroxy group of erythromycin A. However, selective methylation of the 6-hydroxy group is difficult to achieve because erythromycin A has four reactive-hydroxy groups besides 6-hydroxy group as well as a dimethyl amino group which can undergo quaternarization during the methylation reaction.

To deal with such a problem, various methods have been developed for the preparation of clarithromycin.

For example, there has been disclosed a general method of preparing clarithromycin using an erythromycin A 9-oxime derivative, as an intermediate (see EP Patent Nos. 0,158,467; 0,195,960; 0,260,938; and 0,272,110 and International Publication Nos. WO 97/36912 and WO 97/36913). Although this method gives a relatively high yield, it is hampered by a low productivity due to the fact that the process requires a number of reaction steps including the steps of oximization, protecting the oxime group, removing the oxime protection group, and deoximization.

Another general method for preparing clarithromycin has been reported in EP Patent Nos. 0,147,062 and 0,177,696. The method disclosed in EP patent No. 0,147,062 comprises the steps of: protecting the 2-hydroxy and amino groups of erythromycin A with benzyloxycarbonyl groups; methylating the 6-hydroxy group; removing the two benzyloxycarbonyl protecting groups; and methylating the amino group to obtain clarithromycin. However, this method suffers from the problem of a low yield of 13.1 to 18.5% and requires the use of excess benzyloxycarbonyl chloride, besides the difficulty of applying the column chromatographic separation of the product in mass production.

Accordingly, there has existed a need to develop an improved method for preparing clarithromycin.

SUMMARY OF THE INVENTION

It is, therefore, an object of the present invention to provide a method of preparing clarithromycin.

It is another object of the present invention to provide a novel intermediate prepared in said method.

In accordance with one aspect of the present invention, there is provided a method of preparing clarithromycin of formula (I) consisting essentially of the steps of:

(a) preparing erythromycin A N-oxide of formula (II) from erythromycin A;

(b) reacting erythromycin A N-oxide of formula (II) with a methylating agent to obtain 6-O-methylerythromycin A N-oxide of formula (III); and (c) treating 6-O-methylerythromycin A N-oxide obtained in step (b) with a reducing agent to obtain clarithromycin:

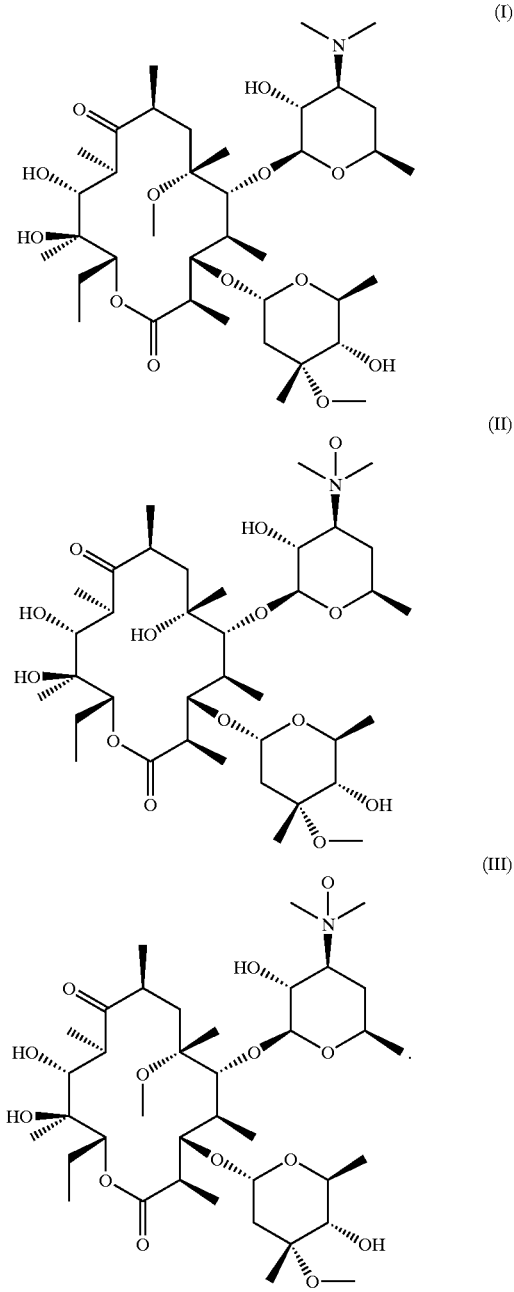

In accordance with another aspect of the present invention, there is provided 6-O-methylerythromycin A N-oxide of formula (III).

DETAILED DESCRIPTION OF THE INVENTION

The compound of formula (I) may be prepared starting from erythromycin A N-oxide as follows:

Step (a)

Erythromycin A N-oxide of formula (II) is produced in a yield of greater than 98% from erythromycin A according to a well-known method [E. H. Flynn et al., *J. Am. Chem. Soc.*, 76, 3121(1954) and P. H. Jones and E. K. Rowly, *J. Org. Chem.*, 33, 665 (1968)].

Step (b)

6O-methylerythromycin A N-oxide of formula (III) is produced by reacting erythromycin A N-oxide of formula (II) with a methylating agent in an organic solvent in the presence of a base.

Exemplary methylating agents which may be suitably used in the present invention are methyl bromide, methyl iodide, dimethyl sulfate, methyl p-toluenesulfonate, methyl methanesulfonate and a mixture thereof. The methylating agent may be used in an amount ranging from 1 to 3 equivalents based on the amount of erythromycin A N-oxide of formula (II).

Exemplary solvents that may be used in the above methylating reaction include N,N-dimethylformamide, N,N-dimethylacetamide, N-methyl-2-pyrrolidone, dimethyl sulfoxide, sulfolane, N,N,N', N', N'',N''-hexamethylphosphoramide, tetrahydrofurane, 1,4-dioxane, 1,2-dimethoxyethane, 1,2-diethoxyethane, 2-methoxyethylether, 2-ethoxyethylether, 1,2-bis(2-methoxyethoxy)ethane, tetraethylene glycol dimethylether, acetone, acetonitrile and a mixture thereof.

Further, a base selected from the group consisting of alkali metal hydrides, hydroxides and alkoxides, e.g., sodium hydride, potassium hydride, sodium hydroxide, potassium hydroxide and potassium t-butoxide, may be suitably used in this process. The base may be used in an amount ranging from 0.9 to 2 equivalents based on the amount of erythromycin A N-oxide of formula (II). The methylating reaction may be carried out at a temperature ranging from −15 to 40° C., preferably from 0° C. to room temperature.

After the completion of the methylating reaction, water is added to the resulting mixture and the mixture is extracted with chloroform. The extract is concentrated and acetone is added to the residue, and then, stirred to precipitate by-products. The resulting mixture is filtered to remove the by-products and the filtrate is concentrated to obtain crude 6-O-methylerythromycin A N-oxide (yield: 67 to 73% and purity: 50 to 57%).

The crude 6-O-methylerythromycin A N-oxide obtained above may be used as is in step (b), or purified by recrystallization from ethylacetate to obtain refined 6-O-methylerythromycin A N-oxide (purity of 83% to 88% and yield of 40 to 44%), which may be further purified by recrystallization from chloroform to obtain 6-O-methylerythromycin A N-oxide crystals having a purity of greater than 95%.

Step (c)

Clarithromycin of formula (I) is prepared by reacting 6-O-methylerythromycin A N-oxide obtained in step (b) with reducing agent in an organic solvent to remove a N-oxide.

Exemplary reducing agents which may be suitably used in the present invention are hydrogen in the presence of a hydrogenation catalyst such as palladium, Raney-nickel or platinum oxide($PtO_2$); a nickel-aluminum alloy(Ni—Al alloy) combined with potassium hydroxide; metallic zinc in the presence of formic acid or acetic acid; sodium hydrogen telluride(NaTeH); samarium iodide($SmI_2$); stannous chloride($SnCl_2$); hexabutylditin($Bu_3SnSnBu_3$); cyclohexene and osmium tetroxide($OsO_4$); and ferrous sulfate, and preferred reducing agents in practicing the present invention are stannous chloride($SnCl_2$), hexabutylditin($Bu_3SnSnBu_3$), a nickel-aluminum alloy combined with potassium hydroxide, and hydrogen in presence of a Raney-nickel or platinum oxide($PtO_2$) catalyst.

In case stannous chloride is used as a reducing agent, solvents such as methanol, ethanol, isopropanol, ethyl acetate, acetonitrile, acetone, tetrahydrofuran, 1,2-dimethoxyethane, dichloromethane, chloroform and a mixture thereof may be used. The amount of stannous chloride used ranges from 1 to 3 molar equivalents based on the amount of 6-O-methylerythromycin A N-oxide of formula (III) and the reaction may be carried out at a temperature ranging from 0° C. to the boiling point of the solvent used, preferably from 10 to 45° C. After the completion of the reaction, clarithromycin may be isolated by (1) neutralizing the reaction mixture with a base such as triethylamine; adding water thereto; and extracting the mixture with an organic solvent; or (2) adding water to the reaction mixture; neutralizing the resulting mixture with a base such as sodium bicarbonate, sodium carbonate, sodium hydroxide solution, and aqueous ammonia; and extracting the mixture with an organic solvent.

In case hexabutylditin is used as a reducing agent, solvents such as ethyl acetate, acetonitrile, acetone, tetrahydrofuran, 1,2-dimethoxyethane and a mixture may be used. Hexabutylditin used in an amount ranges from 1 to 3 molar equivalents based on the amount of 6-O-methylerythromycin A N-oxide of formula (III) and the reaction may be carried out at a temperature ranging from room temperature to the boiling point of the solvent used.

When a Ni—Al alloy is used together with potassium hydroxide as a reducing agent, a mixture of water and a lower alcohol, e.g., methanol and ethanol is employed as a solvent. The amounts of the Ni—Al alloy and potassium hydroxide used are in the range of 0.5 to 3 g and 2 to 20 moles, respectively, based on a mole of 6-O-methylerythromycin A N-oxide of formula (III). The reaction may be carried out at a temperature ranging from room temperature to the boiling point of the solvent used.

When catalytic hydrogenation is carried out as a means of conducting the reaction of step (c), a lower alcohol or a mixture of water and a lower alcohol may be used as a solvent and, a hydrogenation catalyst such as Raney-nickel at a temperature ranging from room temperature to the boiling point of the solvent under a hydrogen atmosphere.

The reaction of step (c) may also be effected using an inorganic reducing agent such as sodium bisulfite($NaHSO_3$), sodium sulfite($Na_2SO_3$), sodium thiosulfate($Na_2S_2O_3$), sodium hydrosulfite($Na_2S_2O_4$), sodium pyrosulfate ($Na_2S_2O_5$), sodium thionate($Na_2S_2O_6$), potassium bisulfite ($KHSO_3$), potassium thiosulfate($K_2S_2O_3$) and potassium pyrosulfate($K_2S_2O_5$). The reaction may be carried out in mixture of water and a lower alcohol such as methanol, ethanol and isopropanol at a temperature ranging from 0° C. to the boiling point of the solvent used. The reducing agent may be used in an amount ranging from 1 to 20 equivalents, preferably from 1 to 4 equivalents based on the amount of 6-O-methylerythromycin A N-oxide of formula (III).

In carrying out the reaction of step (c) using sulfur oxides as a reducing agent, 3'-N-desmethyl-6-O-methylerythromycin A of formula (IV) may be formed as a by-product besides clarithromycin of formula (I). In such a case, the by-products may be converted to clarithromycin by methylating the secondary amine group of the by-product using formic acid and formaldehyde, in accordance with a known method [see Eschweiler & Clarke, *Org. React.*, 5, 290(1945)].

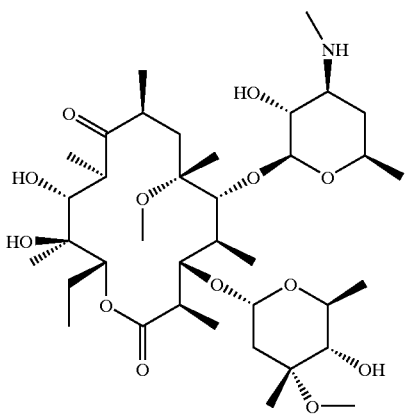

(IV)

The following Reference Example and Examples are intended to further illustrate the present invention without limiting its scope; and the experimental methods used in the present invention can be practiced in accordance with the Reference Example and Examples given herein below, unless otherwise stated.

Further, percentages given below for solid in solid mixture, liquid in liquid, and solid in liquid are on the bases of wt/wt, vol/vol and wt/vol, respectively, unless specifically indicated otherwise.

REFERENCE EXAMPLE

Preparation of Erythromycin A N-oxide 220.2 g(0.3 mol) of erythromycin A was dissolved in a mixture of 1,500 ml of methanol and 1,000 ml of water. 79 ml(0.9 mol) of 35% hydrogen peroxide was added dropwise to the solution at a temperature ranging from 15 to 20° C. and stirred at room temperature for 20 hours in a similar method described in E. H. Flynn et al., *J. Am. Chem. Soc.*, 76, 3121(1954) and P. H. Jones et al., *J. Org. Chem.*, 33, 665(1968). The resulting mixture was concentrated to a half volume under a reduced pressure and extracted successively with 1,000 ml and 500 ml portions of chloroform. The combined chloroform extract was washed with brine, dried over anhydrous magnesium sulfate, and then, concentrated under a reduced pressure to obtain a foamy residue. 1,000 ml of acetone was added to the residue and stirred at room temperature for 3 hours. The crystalline material formed was filtered and dried overnight at 45° C. to obtain 220 g of erythromycin a N-oxide in a yield of 98%.

mp: 218~221° C.(mp in literature: 222~224° C.).

$^1$H-NMR (CDCl$_3$, ppm): δ 5.00(dd, 1H, 13-H), 4.86(d, 1H, 1"-H), 4.50(d, 1H, 1'-H), 3.34(s, 3H, cladinose -OCH$_3$), 3.17(d, 6H, desosamine -N(CH$_3$)$_2$), 1.43(s, 3H, 18-H), 0.82 (t, 3H, 15-H).

MS (m/z): ESI 750[M+1]$^+$

Example 1

Preparation of 6-O-methylerythromycin A N-oxide 75.0 g(0.1 mol) of erythromycin A N-oxide obtained in Reference Example was suspended in a mixture of 450 ml of dimethyl sulfoxide and 450 ml of tetrahydrofuran and cooled to 5° C. Added thereto were 8.1 ml of iodomethane and 7.26 g of 85% potassium hydroxide powder and the mixture was stirred for 1 hour. 1,000 ml of cold water was added to the resulting mixture and extracted successively with 1,000 ml and 500 ml portions of chloroform. The combined extract was washed twice with 500 ml of water, dried over anhydrous magnesium sulfate, and then, concentrated under a reduced pressure. 500 ml of acetone was added to the foamy residue and stirred at room temperature for 5 hours. The resulting mixture was filtered to remove precipitated by-products. The filtrate was concentrated under a reduced pressure to obtain 52.7 g of crude 6-O-methylerythromycin A N-oxide having a purity of 57%.

300 ml of ethyl acetate was added to the crude product and stirred to obtain crystals. The crystals were filtered and dried overnight at 45° C. to obtain 30.3 g of 6-O-methylerythromycin A N-oxide as a crystalline powder having a purity of 88%.

The crystalline powder was recrystallized from chloroform to obtain 20.1 g of the title compound having a purity of greater than 95% in a yield of 27%.

mp: 204~207° C.

IR(KBr, cm$^{-1}$): 3446, 2972, 2938, 1733, 1693, 1462, 1379, 1169, 1111, 1079.

$^1$H-NMR (CDCl$_3$, ppm): δ 5.06(dd, 1H, 13-H), 4.93(d, 1H, 1"-H), 4.55(d, 1H, 1'-H), 4.02(dq, 1H, 5"-H), 3.76(d, 1H, 11-H), 3.73(dd, 1H, 3-H),3.70(d, 1H, 5-H), 3.65(ddq, 1H, 5'-H), 3.38(s, 3H, 3"-OCH$_3$), 3.19(d, 6H, 3'-N(CH$_3$)$_2$), 3.05 (s, 3H, 6-OCH3), 2.91(dq, 1H, 2-H), 2.59(ddq, 1H, 8-H), 1.41(s, 3H, 18-H), 1.12 (s, 3H, 6-CH$_3$), 0.83(t, 3H, 14-CH$_3$).

$^{13}$C-NMR (CDCl$_3$, ppm): δ 221.4(C1=O), 176.2(C9=O), 102.9(C1'), 96.5(C1"), 81.6(C5), 79.0(C6), 78.7(C3), 78.2 (C4"), 77.6(C3'), 77.0(C13), 76.7(C2'), 74.7(C12), 73.1 (C3"), 69.5(C11), 67.4(C5'), 66.3(C5"), 59.1(C8'), 52.8 (C7'), 51.0(C22), 50.1(C8"), 45.7(C8), 45.4(C2), 39.7(C7), 39.6(C4), 37.7(C10), 35.3(C2"), 32.0(C4'), 22.0(C6'), 21.7 (C7"), 21.4(C14), 20.2(C18), 19.1(C6"), 18.4(C19), 16.4 (C21), 16.3(C16), 12.7(C20), 11.0(C15),9.4(C17).

MS (m/z): ESI 764[M+1]$^+$.

Example 2

Preparation of 6-O-methylerythromycin A N-oxide 75.0 g(0.1 mol) of erythromycin A N-oxide obtained in Reference Example was suspended in a mixture of 450 ml of dimethyl sulfoxide and 450 ml of tetrahydrofuran and cooled to 5° C. Added thereto were 8.1 ml of iodomethane and 7.26 g of 85% potassium hydroxide powder and the mixture was stirred for 1.5 hours. 1,000 ml of cold water was added to the resulting mixture and extracted successively with 1,000 ml and 500 ml portions of chloroform. The combined extract was washed twice with 500 ml of water, dried over anhydrous magnesium sulfate, and then, concentrated under a reduced pressure to obtain a foamy residue. 500 ml of acetone was added to the residue and stirred at room temperature for 5 hours. The resulting mixture was filtered to remove precipitated by-products. The filtrate was concentrated under a reduced pressure to obtain 50.4 g of crude 6-O-methylerythromycin A N-oxide having a purity of 55%.

Example 3

Preparation of Clarithromycin by using Stannous Chloride Dihydrate as a Reducing Agent 3.82 g(5 mmol) of 6-O-methylerythromycin A N-oxide obtained in Example 1 was suspended in 30 ml of isopropanol. Added thereto was 2.26 g(2.0 mmol) of stannous chloride dihydrate and the mixture was stirred at a temperature ranging from 30 to 40° C. for 2 hours. A saturated sodium bicarbonate solution was added to the resulting mixture and extracted twice with ethylacetate. The combined organic layer was washed with water, dried over anhydrous magnesium sulfate, and then, concentrated under a reduced pressure to obtain 3.60 g of clarithromycin as a white powder in a yield of 96%.

mp: 220~223° C.(mp in literature: 222~225° C.).

$^1$H-NMR (CDCl$_3$, ppm): δ 5.06(dd, 1H, 13-H), 4.92(d, 1H, 1"-H), 4.44(d, 1H, 1'-H), 4.02(dq, 1H, 5"-H), 3.78(dd, 1H, 3-H), 3.77(d, 1H, 11-H), 3.67(d, 1H, 5-H), 3.57(ddq, 1H, 5'-H), 3.33(s, 3H, 3"-OCH3), 3.20(dd, 1H, 2'-H), 3.07~2.95(m, 2H, 10-H and 4"-H), 3.03(s, 3H, 6-OCH$_3$), 2.87(dq, 1H, 2-H), 2.58(ddq, 1H, 8-H), 2.40(ddd, 1H, 3'-H), 2.37(d, 1H, 2"-Heq), 2.28(s, 6H, 3'-N(CH$_3$)$_2$), 2.00~1.80(m, 3H, 4-H and 7-H$_2$), 1.41(s, 3H, 18-H), 1.13(s, 3H, 6-CH$_3$), 0.85(t, 3H, 14-CH$_3$).

Example 4

Preparation of Clarithromycin by Using Hexabutylditin as a Reducing Agent 3.82 g(5 mmol) of 6-O-methylerythromycin A N-oxide obtained in Example 1 was suspended in 50 ml of tetrahydrofuran. Added thereto was 5.6 ml(2.2 mmol) of hexabutylditin and the mixture was refluxed for 24 hours. The solvent was concentrated under a reduced pressure and isopropyl ether and hexane were added to the residue. The crystals formed were filtered and washed with hexane to obtain 3.55 g of clarithromycin as a white powder in a yield of 95%.

Example 5

Preparation of Clarithromycin by Using Nickel-aluminum Alloy as a Reducing Agent 3.82 g(5 mmol) of 6-O-methylerythromycin A N-oxide obtained in Example 1 was suspended in a mixture of 100 ml of methanol and 50 ml of 1N potassium hydroxide. 5 g of a nickel-aluminum alloy was added thereto over a period of 30 minutes while maintaining the temperature at 35 to 40° C. and stirred for 3 hours. The resulting mixture was diluted with methanol and filtered through a celite pad to remove solids. The filtrate was concentrated under a reduced pressure to remove methanol and the residue was diluted with water. The crystals formed were filtered, washed with water, and then, dried to obtain 3.44 g of clarithromycin as a white powder in a yield of 92%.

Example 6

Preparation of Clarithromycin by Hydrogenation Using a Raney-nickel Catalyst 3.82 g(5 mmol) of 6-O-methylerythromycin A N-oxide obtained in Example 1 was suspended in 100 ml of ethanol. 0.25g of W4 Raney-nickel was added thereto and stirred at a temperature ranging from 40 to 50° C. under a hydrogen atmosphere for 3 hours. The resulting mixture was filtered through a celite pad at 50° C. or higher to remove the spent catalyst. The filtrate was concentrated under a reduced pressure to 30 ml and cooled to room temperature. The crystals formed were filtered and dried to obtain 3.44 g of clarithromycin as a white powder in a yield of 92%.

Example 7

Preparation of Clarithromycin by Using Sodium Bisulfite as Reducing Agent 3.82 g(5 mmol) of 6-O-methylerythromycin A N-oxide obtained in Example 1 was suspended in a mixture of 15 ml of ethanol and 15 ml of water. 1.05 g(10 mmol) of sodium bisulfite was added thereto and stirred at room temperature for 1 hour. The resulting mixture was concentrated, water was added thereto, and then, adjusted to pH 10 with 10% sodium carbonate. The resulting mixture was extracted three times with ethyl acetate, the organic layers were combined, washed with water and brine, and then, dried over anhydrous magnesium sulfate. The solvent was removed under a reduced pressure and the residue obtained was dissolved in 20 ml of ethanol. After adding thereto 0.55 ml of formic acid and 0.8 ml of 35% formaldehyde, the mixture was refluxed for 2 hours. The mixture was concentrated to a half volume and 20 ml of water was added thereto, and then, the resulting mixture was adjusted to pH 11 with 10% sodium carbonate to obtain 3.44 g of clarithromycin as a white powder in a yield of 92%.

Example 8

Preparation of Clarithromycin

The procedure of Example 1 was repeated by using 75.0 g(0.1 mol) of erythromycin A N-oxide obtained in Reference Example, to obtain 54.0 g of crude 6-O-methylerythromycin A N-oxide having a purity of about 54%.

54.0 g of the crude 6-O-methylerythromycin A N-oxide thus obtained was dissolved in 400 ml of dichloromethane and 32.6 g(144 mmol) of stannous chloride dihydrate was added thereto, and then, stirred at room temperature for 1.5 hours. 300 ml of 10% sodium carbonate was added to the resulting mixture and dichloromethane was removed under a reduced pressure. The residue was extracted successively with 400 ml and 200 ml portions of ethyl acetate, the organic layers were combined, washed twice with 300 ml of water, and then, dried over anhydrous magnesium sulfate. The solvent was removed under a reduced pressure, 100 ml of ethanol was added to the residue, refluxed for 30 minutes and stirred at room temperature for 3 hours. The solids formed were collected and dried to obtain 24.0 g of clarithromycin as a white crystal in a yield of 32%.

Example 9

Preparation of Clarithromycin

The procedure of Example 1 was repeated by using 75.0 g(0.1 mol) of erythromycin A N-oxide obtained in Reference Example, to obtain 33.2 g of 6-O-methylerythromycin A N-oxide as a crystalline powder having a purity of about 85%.

33.2 g of the 85% pure 6-O-methylerythromycin A N-oxide was dissolved in a mixture of 70 ml of ethanol and 70 ml of water, 6.52 g(62.6 mmol) of sodium bisulfite was added thereto, and then, stirred at room temperature for 1 hour. The resulting mixture was concentrated to a small volume, water was added to the concentrate, and then, adjusted to pH 10 with 10% sodium carbonate. The resulting mixture was extracted three times with ethyl acetate, the organic layers were combined, washed with water and brine, and then, dried over anhydrous magnesium sulfate. The solvent was removed under a reduced pressure and the residue was dissolved in 80 ml of ethanol. 5.0 ml of formic acid and 7.1 ml of 35% formaldehyde were added to the ethanol solution, and then, refluxed for 2 hours. 200 ml of water was added to the resulting mixture, adjusted to pH 11 with concentrated aqueous ammonia, and then, cooled to room temperature. The solids formed were filtered and dried to obtain 22.5 g of clarithromycin as a white powder in a yield of 30%.

While the embodiments of the subject invention have been described and illustrated, it is obvious that various changes and modifications can be made therein without departing from the spirit of the present invention which should be limited only by the scope of the appended claims.

What is claimed is:

1. A method of preparing clarithromycin of formula (I) consisting essentially of the steps of:

(a) preparing erythromycin A N-oxide of formula (II) from erythromycin A;

(b) reacting erythromycin A N-oxide of formula (II) with a methylating agent to obtain 6-O-methylerythromycin A N-oxide of formula (III); and (c) treating 6-O-methylerythromycin A N-oxide obtained in step (b) with a reducing agent to obtain clarithromycin:

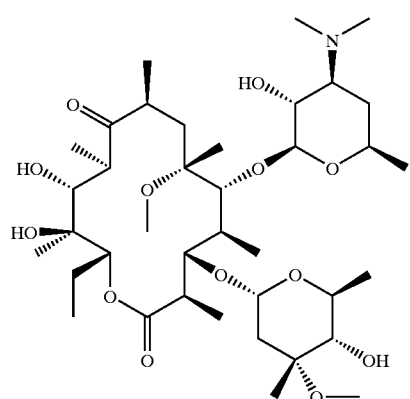

(I)

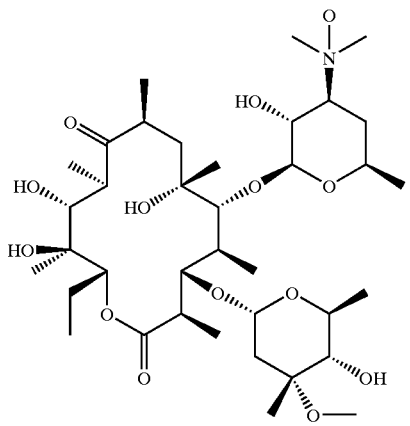

(II)

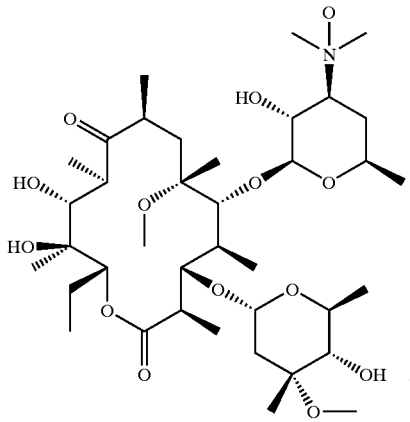

(III)

2. The process of claim 1, wherein step (b) is carried out in an base at a temperature ranging from −15 to 40° C.

3. The process of claim 1, wherein the methylating agent is selected from the group consisting of methyl bromide, methyl iodide, dimethyl sulfate, methyl p-toluenesulfonate, methyl methanesulfonate and a mixture thereof.

4. The process of claim 1, wherein the amount of methylating agent is in the range of 1 to 3 molar equivalents based on the amount of erythromycin A N-oxide.

5. The process of claim 2, wherein the organic solvent is N,N-dimethylformamide, N,N-dimethylacetamide, N-methyl-2-pyrrolidone, dimethyl sulfoxide, sulfolane, N,N,N',N',N'',N''-hexamethylphosphoramide, tetrahydrofurane, 1,4-dioxane, 1,2-dimethoxyethane, 1,2-diethoxyethane, 2-methoxy, 2-methoxyethylether, 2-ethoxyethylether, 1,2-bis(2-methoxyethoxy)ethane, tetraethylene glycol dimethylether, acetone, acetonitrile or a mixture thereof.

6. The process of claim 2, wherein the base is selected from the group consisting of alkali metal hydrides, hydroxides, alkoxides and a mixture thereof.

7. The process of claim 1, wherein the amount of the base is in the range of 0.9 to 2 molar equivalents based on the amount of erythromycin A N-oxide.

8. The process of claim 1, wherein the reducing agent is selected from the group consisting of hydrogen in the presence of a hydrogenation catalyst; a nickel-aluminum alloy(Ni—Al alloy) combined with potassium hydroxide; metallic zinc in the presence of formic acid or acetic acid; sodium hydrogen telluride(NaTeH); samarium iodide ($SmI_2$); stannous chloride($SnCl_2$); hexabutylditin ($Bu_3SnSnBu_3$); a mixture of cyclohexene and osmium tetroxide($OsO_4$); ferrous sulfate; $NaHSO_3$; $Na_2SO_3$; $Na_2S_2O_3$; $Na_2S_2O_4$; $Na_2S_2O_5$; $Na_2S_2O_6$; $KHSO_3$; $K_2S_2O_3$; $K_2S_2O_5$; and a mixture thereof.

9. The process of claim 1, wherein the reducing agent is selected from the group consisting of stannous chloride ($SnCl_2$); hexabutylditin($Bu_3SnSnBu_3$); a nickel-aluminum alloy combined with potassium hydroxide; and hydrogen in the presence of a Raney-nickel or platinum oxide($PtO_2$) catalyst.

* * * * *